(12) United States Patent
Lisi

(10) Patent No.: US 6,380,198 B1
(45) Date of Patent: Apr. 30, 2002

(54) USE OF FLUNARIZINE FOR THE TOPICAL TREATMENT OF GLAUCOMA

(75) Inventor: Giuseppe Lisi, Milan (IT)

(73) Assignee: Laboratoire Medidom S.A., Geneva (CH)

( * ) Notice: Subject to any disclaimer, the term of this patent is extended or adjusted under 35 U.S.C. 154(b) by 0 days.

(21) Appl. No.: 09/509,912

(22) PCT Filed: Oct. 6, 1998

(86) PCT No.: PCT/IT98/00266

§ 371 Date: Apr. 4, 2000

§ 102(e) Date: Apr. 4, 2000

(87) PCT Pub. No.: WO99/18963

PCT Pub. Date: Apr. 22, 1999

(30) Foreign Application Priority Data

Oct. 10, 1997 (IT) ........................................ RM97A0613

(51) Int. Cl.[7] .............................................. A61K 31/50
(52) U.S. Cl. .................................. 514/252.12; 514/912
(58) Field of Search ............................ 514/252.12, 912

(56) References Cited

FOREIGN PATENT DOCUMENTS

WO 9323082 11/1993

OTHER PUBLICATIONS

Database Biosis, Biosciences Information Service, Philadelphis, PA, k. Fujita et al., "Effects of flunarizine on primary open angle and low tension glaucomas".
Cellini et al., "The use of flunarizine in the management of low–tension glaucoma: A Color Doppler study", ACTA Ophthalmologica Scandinavica, vol. 224, No. Supp., Mar. 1997, pp. 57–58, XP002091121.

Primary Examiner—Zohreh Fay
(74) Attorney, Agent, or Firm—Hedman & Costigan, P.C.

(57) ABSTRACT

Use of flunarizine, a calcium channel blocking agent known for use as cerebral and peripheral vasodilator, in the treatment of glaucoma by topical administration. Differently from other calcium channel blockers already tested for use as antiglaucoma agents, flunarizine is highly active in lowering the intraocular pressure when administered by the topical ophthalmic route. The invention also comprises anti-glaucoma preparations containing flunarizine, or combinations of flunarizine with beta-blockers such as timolol.

11 Claims, 2 Drawing Sheets

USE OF FLUNARIZINE FOR THE TOPICAL TREATMENT OF GLAUCOMA

This Application is a 371 of PCT/IT98/00266, filed on Oct. 6, 1998.

SPECIFICATION

The present invention concerns the use of flunarizine for the topical treatment of glaucoma. More specifically, this invention relates to the use of flunarizine, a calcium channel blocking agent known and employed as cerebral and peripheral vasodilator, in a new indication as an antiglaucoma agent for topical ophthalmic treatment.

As it is known, glaucoma is a pathological ophthalmic condition the underlying causes of which are not well understood at present. This condition is usually shown by a progressive increase of the intraocular pressure, leading to severe impairment of the eye structures, in particular to damage to the optic nerve disc and to decrease in the visual field, finally resulting in optic atrophy. The disease is generally connected to an insufficient outflow of aqueous humour from the eye, although other causes, such as, e.g., the production of aqueous humour and the episcleral veins pressure, take part in the regulation of the intraocular pressure.

The rationale of the pharmacological therapy presently in use is to lower the intraocular pressure. The drugs currently used to that aim, divided into classes according to their mechanism of action, are beta-blockers (such as timolol, betaxolol, levobunolol), sympathomimetics (such as epinephrine and dipivephrine), parasympathomimetics or miotics (such as pilocarpine and acetylcholine) and carbonic anhydrase inhibitors (such as acetazolamide and dichlorphenamide). Besides the foregoing drugs well established in use, the search for agents having less side effects and longer lasting activity has lead to evaluate, more recently, the possibility of using for the treatment of glaucoma another class of drugs, i.e. the calcium blocking agents. The latter, also known as "calcium entry blockers" or "calcium antagonists", are currently used as vasodilators and in the treatment of cardiac affections. For such indications, the most widespread calcium antagonists are, e.g., nifedipine, diltiazem and verapamil.

The role of calcium in the dynamics of aqueous humour and in the control of intraocular pressure has not yet been entirely clarified, although it is known that the production and the outflow of aqueous are modulated also by calcium. As concerns the formation of aqueous, it is to be noted, firstly, that the hydrostatic component due to the arterial pressure and to the pressure of the vessels feeding the ciliary body is calcium-dependent, as it is confirmed by the known systemic vascular action of calcium antagonists. Further, the osmotic pressure due to ionic secretion at the level of the non-pigmented ciliary epithelium is likely to be modulated by calcium, as hypothesised by Abelson et al. (Abelson M. B., Gilbert C. M., Smith L. M., Sustained reduction of intraocular pressure in humans with the calcium channel blocker verapamil, Am. J. Ophthamol. 105; 155 (1988)).

As far as the outflow of the aqueous humour is concerned, calcium ions play a direct role in modulating the pressure of episcleral veins, and some studies suggest that calcium influences the outflow capacity, by maintaining the structural integrity of the trabecuale and of the exterior wall of the Schlemm's canal.

In spite of the foregoing suggestions several experimental works, both on animal models and clinical, and involving both systemic and topical administration, reported contradictory results about the activity of calcium channel blockers in the therapy of glaucoma. For instance, Monica et al. (Monica M. L., Hesse R. J., Messerli F. H., The effect of a calcium-channel blocking agent on intraocular pressure, Am. J. Ophthalmol. 96, 814 (1983)) reports that the oral administration of nitrendipine to patients with moderate hypertension but with normal intraocular pressure slightly lowered the latter, while Beatty and co-workers (Beatty J. F., Krupin T., Nichols P. F., Elevation of intraocular pressure by calcium-channel blockers, Arch. Ophthalmol. 102; 1072, (1984)) did not evidence any effect upon oral administration of verapamil to rabbits, and did even report an increase in the intraocular pressure upon topical administration. More recently, for instance, Payene and coworkers (Payene, L. J., Slagle T. M., Cheeks L. T., Effect of calcium-channel blockers on intraocular pressure, Ophthalmic Res. 22; 337, (1990)) obtained a reduction in the intraocular pressure upon systemic administration of verapamil or nifedipine to rabbits, but did not detect any significant effect upon topical administration of the same agents or of diltiazem by the topical route.

In general, however, at least as far as verapamil is concerned, it may be said that the administration of this drug to man normally results in a reduction of the intraocular pressure. A more consistent reduction upon topical administration has been explained, in particular, by a work of Ettl et al. (Ettl A., Daxer A., Hoffmann U., Calcium channel blockers in the management of low-tension and open-angle glaucoma, Am. J. Ophthalmol. 116; 778, (1993)). These authors have detected, in the rabbit eye, verapamil levels 200 times higher than the levels obtainable by systemic administration.

Accordingly, the use of verapamil in the treatment of ocular hypertension is the object of the international PCT application No. WO 92/07563, filed by Abelson (i.e., the first author cited above) et al. A later publication in the name of the same author is the international application No. WO 96/03986, concerning the treatment of a particular form of glaucoma, referred to as low-tension glaucoma. This pathology is characterised by an intraocular pressure which is almost normal, in spite of the fact that all of the other symptoms of glaucoma are present. In the latter document the therapeutic proposal is generically extended to all calcium-antagonists, many representatives of which are mentioned in a preliminary list. However, the only example of active agent disclosed in the document and supported by experimental data is verapamil.

Another calcium blocking agent that was specifically proposed for use, in a patent document, in the treatment of intraocular hypertension is diltiazem (French patent No. 2593395, published in 1987), while a list of more than one hundred calcium antagonists is presented in the international PCT application No. WO 93/23082. The latter concerns, for use in the treatment of glaucoma, a combination of a compound which lowers the intraocular pressure (i.e., a conventional antiglaucoma agent) and a calcium channel blocking agent. The disclosure does not contain any specific example of preferred combination, nor any experimental detail regarding the activity of any combination.

Some experimental trials on verapamil also allowed to ascertain that the ophthalmic use of the said agent causes an undesirable swelling of the cornea. (Green K., Cheeks L., Hull D. S., Effects of calcium channel blockers on rabbit corneal endothelial function, Curr. Eye Res. 13; 401–408, (1994)). This is particularly critical if one considers the use for the treatment of a chronic condition as is, actually, glaucoma.

Although the entire class of calcium antagonists has already been considered for its potential use in the treatment of glaucoma, there does not seem to have been evidenced the particular activity, against this type of pathologies, of a specific agent belonging to the said class, i.e. flunarizine. It has now been found, and it is the subject-matter of this invention, that the specific calcium antagonist flunarizine, when administered through the topical ocular route, is able to lower the intraocular pressure in a surprisingly more marked way than the other calcium antagonists so far proposed and tested for the therapy of glaucoma.

Within the frame of the studies connected with this invention, it has also been found that some known receptors, referred to as σ receptors, are localised in the ocular region, in particular in the ciliary body and in the iris, and that some specific "ligands", having a σ-agonist activity, significantly lower the ocular pressure. Since it has been experimentally found that flunarizine shows a σ-agonist activity which is far higher than the activity of other calcium antagonists, this property may explain the unexpectedly greater activity of flunarizine in lowering the intraocular pressure, if it is hypothesised that such activity is exerted according to mechanisms of action that are at least partially different from the other calcium blocking agents.

In order to identify the presence of a receptor sites in the eye the technique of "receptor binding" has been exploited. The latter has been carried out on cell membranes obtained from the irido-ciliary body complex. The irido-ciliary body complex had been explanted, after sacrifice, from male albino rabbits of the New Zealand strain. The tissue was homogenised in buffer and a fraction rich in cell membrane proteins was isolated, obtained by centrifugation. The concentration of total proteins has been evaluated by the method of Lowry (Lowry, J. Biol. Chem. 193; 265 (1951)). Aliquots of the said fraction of the homogenate containing 300 $\mu$g of total proteins were incubated with scalar amounts of [$^3$H] (+)-pentazocine (which is used, for experimental purposes only, as a a ligand). The reaction was carried out at 37° C. for 150 minutes and then, after filtering, the radioactivity left on the filters was measured by liquid scintillation. The apparent dissociation constant (Kd) and the total number of receptors were determined, and it was thus ascertained that [$^3$H])(+)-pentazocine selectively binds to receptor sites present in the iridociliary body region of the rabbit. On the basis of the present scientific knowledge, the said receptors appear to be of the type σ-1.

Further, "competitive binding" assays carried out with a constant is amount of [$^3$H](+)-pentazocine and scalar amounts of (+)-N-allil-nor-meth-azocine (NANM) (which is used, for experimental purposes only, as a σ ligand), showed that the latter shift the radioactive ligands from the receptor sites. It has also been observed, by analysing the Hill coefficient, that NANM interacts with one only class of a receptor sites.

In the frame of the same research it has been found that σ-agonist agents show an ocular anti-hypertensive activity. A 1% preparation of NANM was administered (50 $\mu$l) in the conjunctival fornix of the right eye of male albino rabbits of the New Zealand strain, after measuring the (baseline) intraocular pressure. Upon measuring again the intraocular pressure 60, 120, 180 e 240 minutes after the instillation, it has been ascertained that the intraocular pressure was significantly reduced (p<0.01) 60 minutes after the instillation, in comparison with the formulation containing the vehicle only.

Lastly, as it was pointed out before, studies of receptor binding carried out with flunarizine (some of which are presented in the following) have shown that flunarizine has an affinity for σ-1 receptors which is not even comparable to the affinity shown by the other calcium channel blocking agents tested.

Another advantageous aspect distinguishing flunarizine from the other calcium channel blocking agents proposed so far for the topical treatment of glaucoma is, as it has now been found, that flunarizine does not show any side effect of corneal swelling.

Therefore, the present invention specifically provides the use of flunarizine, optionally in the form of a pharmaceutically acceptable salt, for the topical treatment of glaucoma, i.e. the use of flunarizine, or of a pharmaceutically acceptable salt thereof, in the manufacture of a topical ophthalmic medicament for the treatment and/or the prophylaxis of glaucoma. In general, the topical administration of flunarizine may take place by using a preparation in the form of an aqueous solution or suspension, or in the form a gel, an ointment or a cream in a pharmaceutically acceptable ophthalmic vehicle, or in the form of an erodible ocular insert or of a "reservoir" system with a polymer membrane, to be placed in the conjunctival sac.

The concentration of flunarizine in an ophthalmic vehicle may range from 10 $\mu$g/ml to 5 mg/ml, i.e. from 0.001 to 0.500% by weight. The optimal concentration is chosen firstly on the basis of the dosage to be administered: in the case of use in eye-drop form, for instance, one drop should contain a sufficient amount of flunarizine for the drop to be effective as such or when instilled twice (i.e., two drops). Other criteria for the choice of the concentration are the ocular tolerability (it should be considered that the conjunctival sac, into which the ophthalmic preparation is to be instilled, has a limited capacity) and the stability of the active ingredient. The preferred concentration for an aqueous solution formulation (eye-drops) is 0.050% by weight, and preferably the product is present in the form of the corresponding hydrochloride salt (optimal concentration of flunarizine hydrochloride: 0.052%).

According to a particularly preferred embodiment of this invention, the anti-glaucoma activity of the proposed ophthalmic preparation is further enhanced by the presence, in combination with flunarizine, of an effective amount of a beta-blocking agent. The class of beta-blockers (or β-adrenergic blockers), referred to in the foregoing, represents to date the most widespread class of anti-glaucoma agents. These agents are used in the topical treatment of chronic open angle glaucoma and, more generally, in the treatment of intraocular hypertension. Their mechanism of action mainly consists in reducing the production of the aqueous humour, and therefore the unexpected enhanced activity of the proposed combination of flunarizine (which has been found to be active in increasing the outflow of aqueous) with a beta-blocker may reasonably be explained in terms of a complementarity of the two actions.

Preferably, the concentration of beta-blocking agent in the combination according to the invention is from 0.1 to 2.5% by weight, and most preferably said beta-blocking agent is timolol or a pharmaceutically acceptable salt thereof, A vehicle that may be employed in an eye-drop preparation according to the invention is the simple physiological saline solution containing 0.9% by weight of sodium chloride. Such solution is isotonic with respect to the tear fluid, and therefore it is well tolerated by the eye. However, also hypotonic solutions or suspensions may be employed, as it is known that these preparations are well tolerated by the ocular tissues.

Other excipients may be added to the composition of the invention in order to adjust the tonicity of the solutions or suspensions, so as to stabilise the active ingredient(s) and to increase the tolerability of the preparation. Specifically, any buffers should maintain the pH into the range 4–8. For instance, the above saline solution may be buffered with any one of the buffers well known in the pharmaceutical art for ophthalmic use, such as, e.g., phosphate buffer, or trizma buffer (i.e., tri-hydroxymethyl amino methane), so as to obtain a physiological pH, in the range of 7.0–7.4. Further, the solution may also have an osmolarity in the physiological range (295–305 mOsm/l). This allows to obtain a better ocular tolerability, In addition, the formulation may advantageously contain an antioxidant, such as, e.g., gallates, ascorbic acid, superoxide dismutase (SOD), BHT, sodium metabisulphite, tocopherols, BHA, nordihydroguaiaretic acid, ascorbic acid esters, dimethylthiourea and the like.

The tolerability may be further enhanced by means of other excipients such as cyclodextrins, polysorbate 80 (or Tween 80), dextrane (e.g., dextrane 70), polyethylene glycol (e.g. PEG 400), poloxamers and other similar agents. The formulation may include viscosifying/thickening agents such as methylcellulose, polyvinyl alcohol, glucosamine glucans, polyvinyl pyrrolidone and the like, in order to increase the ocular bioavailability, the stability and the tolerability of the active ingredient(s).

The ocular bioavailability of flunarizine may be further enhanced by the addition of substances which increase the corneal permeation of the drug, such as, e.g., dimethyl sulphoxide, taurocholates, membrane phospholipides, benzalkonium chloride and other surface active agents for ophthalmic use (such as disodium lauryl sulphosuccinate).

Lastly, in the preparations to be packaged in multidose bottles compositions a preservative with antimicrobial activity will have to be added, in order to prevent contamination of the product. Such agent may be chosen among the preservative agents well known for this use in the pharmaceutical art.

Products to be administered in the form of suspensions should contain suitable agents such as carboxymethyl cellulose and the like. In the event that the preparation is to be employed in the form of an ointment, a gel or a cream for ophthalmic use, flunarizine will be admixed with carriers such as polyethylene glycols, polyacrylates, polyethylene oxides, fatty acids and alcohols or lanolin, paraffin and other similar products. Suitable ingredients for the production of emulsions or microemulsions may be chosen among the following: diethylene glycol-monobutyl ether, di(ethylene glycol) buthyl ether, caprylic acid ethyl ester, oleic acid ethyl ester, soybean oil, hexadecane, tributyrin, ethylene glycol-monobutyl ether, 1-hexadecene, n-heptane, 1-heptene, Tween 80, PEG, poloxamers, polyoxyethylene ethers.

The dosage of the main active ingredient of the invention, to be administered by the topical route, may vary from about 20 μg to about 200 μg per day for each eye. The prescription dosage of the ophthalmic preparations based on flunarizine will depend on the daily dose that will be necessary to achieve the therapeutic effect and, obviously, on the specific formulation employed. Ophthalmic solutions or suspensions will require from 1 to 4 instiliations per day; ointments, gels and creams will require 1 or 2 applications; solid inserts with polymeric matrix, either biodegradable or not, will require one only administration per day.

The present invention further concerns compositions which allow the administration of flunarizine through the topical ophthalmic route, and specific ophthalmic compositions for use in the treatment and/or in the prophylaxis of glaucoma comprising, as an active ingredient, a therapeutically effective amount of flunarizine. A group of preferred compositions have the following formulation (wherein all percentages are by weight):

| | |
|---|---|
| flunarizine hydrochloride | 0.059% |
| (corresponding to 0.05% flunarizine) | |
| sodium chloride | 0.10–0.80% |
| trizma buffer | 0.02–0.20% |
| PEG 400 | 1.00–6.00% |
| Tween 80 | 2.00–12.00% |
| sodium metabisulphite | 0.01–0.20% |
| propyl gallate | 0.01–0.50% |
| EDTA | 0.005–0.20% |
| purified water | q.s. to 100% | optionally comprising further pharmaceutically acceptable ingredients.

In a particularly preferred embodiment of this invention, the compositions for use in the treatment and/or in the prophylaxis of glaucoma further contain from 0.1 to 2.5% by weight of a beta-blocking agent, the latter being by preference timolol or a pharmaceutically acceptable salt thereof, such as timolol maleate.

Some specific embodiments of the invention are described below for merely illustrative purposes, together with the results of the experimental studies carried out on the proposed anti-glaucoma agent, including comparative tests with other calcium-blocking agents.

EXAMPLE 1

Ophthalmic Solution Based on Flunarizine

A composition according to the invention that turned out to be particularly effective (the performance of which was experimentally evaluated as it is partly reported further on) has the following composition (the percentages being given by weight):

| | |
|---|---|
| flunarizine hydrochloride | 0.059% |
| (corresponding to 0.050% flunarizine) | |
| sodium chloride | 0.485% |
| trizma buffer | 0.100% |
| PEG 400 | 2.500% |
| Tween 80 | 5.000% |
| sodium metabisulphite | 0.050% |
| propyl gallate | 0.050% |
| EDTA | 0.010% |
| purified water | q.s. to 100% |

The above composition is suitable for being packaged in single dose containers; in the event that a multidose packaging is desired, a preservative (such as, e.g., benzalkonium chloride) will have to be added in order to maintain the sterility of the product for the whole period of use.

EXAMPLE 2

Ophthalmic Microemulsion Based on Flunarizine

A composition suitable for use as an ophthalmic ointment was prepared according to the formulation given below (weight percentages):

| | |
|---|---|
| flunarizine hydrochloride | 0.059% |
| (corresponding to 0.050% flunarizine) | |
| trizma buffer (to pH 7.20) | 0.100% |
| PEG 400 | 10.000% |
| soybean oil | 2.00% |
| Tween 80 | 20.000% |
| sodium metabisulphite | 0.050% |
| sorbitol | 2.057% |
| propyl gallate | 0.050% |
| purified water | q.s. to 100% |

As a tonicity adjusting agent, 455 mg of sodium chloride per 100 ml (i.e. 0.455 wt. %) may be used in place of the above amount of sorbitol,

EXAMPLE 3

Ophthalmic Emulsion Based on Flunarizine

An ophthalmic product similar to that shown in the previous example, but having a coarser size of the drops of the dispersed phase, was obtained excluding the soybean oil from the composition, according to the following formulation (weight percentages):

| | |
|---|---|
| flunarizine hydrochloride | 0.059% |
| (corresponding to 0.050% flunarizine) | |
| trizma buffer (to pH 7.20) | 0.100% |
| PEG 400 | 2.000% |
| Tween 80 | 7.000% |
| sodium metabisulphite | 0.050% |
| sorbitol | 2.014% |
| propyl gallate | 0.050% |
| purified water | q.s. to 100% |

As an alternative to sorbitol as a tonicity adjusting agent, the composition may include 433 mg of sodium chloride per 100 ml (i.e. 0.433 wt. %).

EXAMPLE 4

Ophthalmic Solution Based on a Combination of Flunarizine and Timolol

A particularly preferred composition according to the invention was obtained by adding to the formulation of Example 1 a sufficient amount of imolol maleate to achieve a concentration of 0.5% by weight of timolol in the verall composition (corresponding to about 0.68% by weight of timolol maleate). The concentrations of the other ingredients were the same as specified above for Example 1.

Similarly, also the formulations given in Examples 2 and 3 can be modified with the addition of a proper amount of timolol maleate. Also in this case, it is preferred to obtain a concentration of 0.5% by weight of timolol in the overall composition.

Experimental Results

An isotonic solution, buffered and viscosified according to the formulation of Example 1, but having variable concentrations of flunarizine (ranging from 0.01% to 0.1% by weight), was generally referred to as MEG 01 in the experimental work the results of which are set forth below. The experimentation also considered combinations of flunarizine and beta-blocking agents formulated as shown for timolol in Example 4. The combination of flunarizine and timolol was referred to as MEG 02. Some of the said experimental results are also shown in the graphs of the accompanying drawings, wherein.

Figure 1:
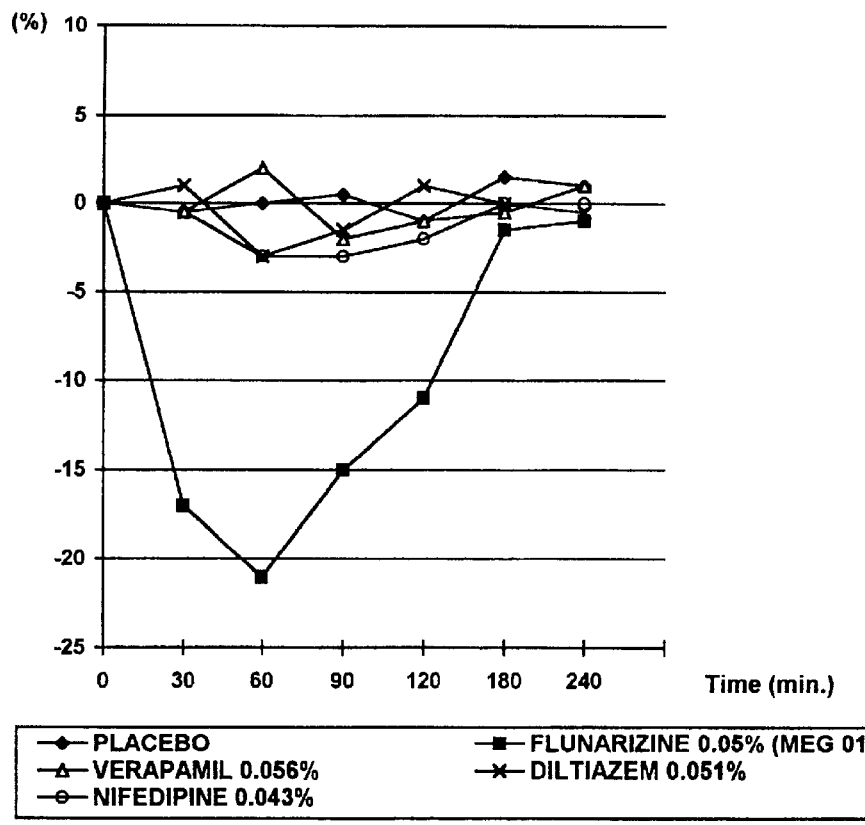
FIG. 1 shows the percent reduction in the intraocular pressure obtained upon instillation of flunarizine in the eyes of rabbits with hypertension, in comparison with the corresponding reduction obtained with the instillation of placebo and with the instillation of other calcium antagonists.

Pharmacodynamic Studies a. Study on Rabbits with Normal Intraocular Pressure

The effects of the agent of the invention on the intraocular pressure of rabbits showing normal baseline intraocular pressure were evaluated in comparison with the action of a placebo, and with that of various other calcium channel blocking agents. Female pigmented rabbits of the Vienna Blue strain were used (supplied by Charles River Italiana, of Calco (CO)). The age of the animals at the time of starting the experimentation was 9 weeks, and their weight was 2.0–2.5 kg.

The choice of a species with pigmented iris is due to the fact that the latter represents a reliable model for the evaluation of possible modifications of the intraocular pressure caused by the products under test. The strain chosen is genetically defined, so as to limit to a minimum the variability of the biological characteristics between one animal and the other.

The animals were kept in rooms maintained under constant and controlled conditions of temperature and humidity, illuminated for 12 hours a day with artificial light and with continuous renovation of the air. The feed consisted of a standard diet having a constant and known composition, and both feed and water were available ad libitum during the whole period of the test. The rabbits were stabled for 21 days before starting the test, so as to allow a sufficient acclimatation and to suitably evaluate the health conditions of the rabbits. Each experimental group consisted of 4 animals, which were allotted to the treatment groups in a randomised way.

Each different group of animals received, by instillation in the right conjunctival fornix, 50 μl of the following products:
a) eyerops of MEG 01, containing 0.050 wt. % flunarizine (0.052 wt. % flunarizine hydrochloride);
b) placebo solution (i.e., the vehicle of MEG 01);
c) eye-drops containing 0.056 wt. % verapamil in the vehicle of MEG 01;
d) eye-drops containing 0.051 wt. % diltiazem in the vehicle of MEG 01;
e) eye-drops containing 0.043 wt. % nifedipine in the vehicle of MEG 01.

The weight concentrations of the various agents under test are chosen so as to correspond to the same molar concentration.

The pressure in the treated eye was measured by flattening tonometer (TonopenXL®, Mentor), 15 minutes before the instillation of the eyerops (time 0) and then 30, 60, 90, 120, 180 and 240 minutes after. As a local anaesthetic, 5 minutes before carrying out each measurement 25 μl of a commercial ophthalmic solution containing 0.4% oxybuprocaine hydrochloride (Novesine®, Sandoz) was instilled. To carry out the measurement the rabbits were placed in a suitably designed cage, that prevents any sudden movement of the animal under test.

For each animal and at each of the times listed above the average of three subsequent measurements was calculated and recorded, each one said measurements being made after 1 minute from the previous one. The intraocular pressure values at the various times were compared with the values obtained before the treatment, by means of the Student's "t" test. The comparisons between different groups were made by processing the data by the variance analysis (ANOVA) and, where possible, by the Student's "t" test for the comparison of two different experimental groups. Values of $p<0.05$ were considered to be statistically significant.

The following table shows the values of intraocular pressure determined on each one of the animals treated, as well as the average values for each test group (± standard deviation).

significant modification in the intraocular pressure. In the latter case, the pressure values measured upon administration of the eye-drops are not statistically different from the values recorded before the instillation (time 0: 15 minutes before the administration).

Furthermore, neither the verapamil formulation nor the diltiazem formulation, both using the same vehicle as MEG 01, did produce any intraocular pressure decrease with respect to the placebo. Some minor reduction could be detected with the administration of nifedipine, but this effect appears to be negligible in comparison with the response obtained with MEG 01 containing 0.050 wt. % flunarizine.

Another series of tests was carried out on rabbits with normal base-line intraocular pressure in order to compare the activity of flunarizine with that of the proposed combination of flunarizine with a beta-blocking agent, and with the activity of a beta-blocking agent alone.

The following well-known beta-blockers were tested: timrolol (which is a non-selective beta-blocker, being active both on $\beta_1$ and on $\beta_2$ adrenergic receptors), betaxolol (a cardioselective beta-blocker, active on the $\beta_1$ adrenergic

TABLE 1

Intraocular pressure in rabbits with normal pressure treated with the tested agents

| Rabbit No. | Eye | Intraocular pressure (mmHg) at the time (min) | | | | | | |
|---|---|---|---|---|---|---|---|---|
| | | 0 | 30 | 60 | 90 | 120 | 180 | 240 |
| Eye-drops with 0.050% flunarizine (MEG 01) | | | | | | | | |
| 01 | RE | 17 | 15 | 14 | 15 | 15 | 15 | 17 |
| 02 | RE | 16 | 14 | 13 | 14 | 14 | 15 | 16 |
| 03 | RE | 14 | 13 | 12 | 12 | 14 | 14 | 16 |
| 04 | RE | 16 | 12 | 12 | 14 | 14 | 14 | 16 |
| average ± S.D. | | 15.7 ± 1.2 | 13.5 ± 1.3 | 12.7 ± 0.95 | 13.7 ± 1.2 | 14.2 ± 0.5 | 14.5 ± 0.5 | 16,2 ± 0,5 |
| Placebo | | | | | | | | |
| 05 | RE | 15 | 16 | 16 | 15 | 15 | 16 | 16 |
| 06 | RE | 16 | 15 | 14 | 16 | 16 | 17 | 17 |
| 07 | RE | 17 | 15 | 16 | 16 | 16 | 17 | 17 |
| 08 | RE | 15 | 15 | 16 | 16 | 18 | 15 | 17 |
| average ± S.D. | | 15.7 ± 0.9 | 15.2 ± 0.5 | 15.5 ± 1.0 | 15.7 ± 0.5 | 15.7 ± 0.5 | 16.2 ± 0.9 | 16.7 ± 0.5 |
| Eye-drops with 0.056% verapamil | | | | | | | | |
| 09 | RE | 17 | 16 | 15 | 15 | 16 | 16 | 17 |
| 10 | RE | 15 | 14 | 14 | 13 | 13 | 16 | 15 |
| 11 | RE | 16 | 17 | 15 | 15 | 16 | 17 | 17 |
| 12 | RE | 16 | 15 | 15 | 15 | 16 | 16 | 17 |
| average ± S.D. | | 16 ± 0.8 | 15 ± 1.3 | 14.7 ± 0.5 | 14 ± 1.0 | 15.7 ± 0.5 | 16.2 ± 0.5 | 16.5 ± 1.0 |
| Eye-drops with 0.051% diltiazem | | | | | | | | |
| 13 | RE | 15 | 14 | 14 | 14 | 15 | 15 | 16 |
| 14 | RE | 16 | 15 | 14 | 14 | 15 | 16 | 16 |
| 15 | RE | 18 | 17 | 17 | 16 | 16 | 17 | 17 |
| 16 | RE | 18 | 15 | 13 | 15 | 16 | 17 | 17 |
| average ± S.D. | | 16.7 ± 1.5 | 15.2 ± 1.2 | 14.7 ± 0.9 | 14.7 ± 0.9 | 15 ± 0.5 | 16.2 ± 0.95 | 16 ± 0.6 |
| Eye-drops with 0.043% nifedipine | | | | | | | | |
| 17 | RE | 16 | 15 | 14 | 16 | 16 | 17 | 17 |
| 18 | RE | 15 | 15 | 13 | 15 | 16 | 15 | 17 |
| 19 | RE | 14 | 13 | 13 | 15 | 16 | 15 | 14 |
| 20 | RE | 18 | 16 | 15 | 16 | 16 | 17 | 18 |
| average ± S.D. | | 15.7 ± 1.7 | 14.7 ± 1.2 | 13.7 ± 0.9 | 15.5 ± 0.6 | 16.0 ± 1.5 | 16.5 ± 1.7 | 16 ± 0 |

As it is shown by the previous table, the MEG 01 eye-drops (containing 0.050% flunarizine) produced a significant reduction in the intraocular pressure after one hour from the administration, while a product consisting in the corresponding vehicle without flunarizine did not cause any receptors only) and carteolol (which is not selective, but is endowed with an intrinsic sympathomimetic activity). The tests were carried out according to the same experimental protocol described above, treating each different group of animals with the following compositions:

f) eye-drops of MEG 02, containing 0.050 wt. % flunarizine (0.052 wt. % flunarizine hydrochloride) in combination with 0.5 wt. % timolol (0.68 wt. % timolol maleate);

g) eye-drops containing 0.050 wt. % flunarizine and 0.5 wt. % betaxolol in the vehicle of MEG 02;

h) eye-drops containing 0.050 wt. % flunarizine and 2.0 wt. % carteolol in the vehicle of MEG 02.

The results of this series of tests, obtained and processed in the same way as those shown in Table 1, are presented in the following table. In order to make any comparison easier, the data obtained with flunarizine alone and with the placebo, i.e. with the groups of animals a) and b) of the previous experiment, are shown again in the following table.

the performance of the combination was better than that of flunarizine alone.

b. Study on Rabbits with Ocular Hypertension

Rabbits of the same type as those described in the previous section were used for the following tests. The rabbits had been preliminarily treated in the same way, and the stabling conditions were the same.

The experimental increase in the intraocular pressure was induced by administration of σ-chymotrypsin. In the rabbit, the injection of this enzyme in the posterior chamber causes, after one month from the administration, an effect of ocular hypertension. This experimental model is widely used, and has often been employed in order to evaluate the activity of various antiglaucoma agents.

TABLE 2

Intraocular pressure in rabbits with normal pressure treated with the tested agents

| Rabbit No. | Eye | Intraocular pressure (mmHg) at the time (min) | | | | | | |
|---|---|---|---|---|---|---|---|---|
| | | 0 | 30 | 60 | 90 | 120 | 180 | 240 |
| Eye-drops with 0.050% flunarizine (MEG 01) | | | | | | | | |
| 01 | RE | 17 | 15 | 14 | 15 | 15 | 15 | 17 |
| 02 | RE | 16 | 14 | 13 | 14 | 14 | 15 | 16 |
| 03 | RE | 14 | 13 | 12 | 12 | 14 | 14 | 16 |
| 04 | RE | 16 | 12 | 12 | 14 | 14 | 14 | 16 |
| average ± S.D. | | 15.7 ± 1.2 | 13.5 ± 1.3 | 12.7 ± 0.95 | 13.7 ± 1.2 | 14.2 ± 0.5 | 14.5 ± 0.5 | 16,2 ± 0,5 |
| Placebo | | | | | | | | |
| 05 | RE | 15 | 16 | 16 | 15 | 15 | 16 | 16 |
| 06 | RE | 16 | 15 | 14 | 16 | 16 | 17 | 17 |
| 07 | RE | 17 | 15 | 16 | 16 | 16 | 17 | 17 |
| 08 | RE | 15 | 15 | 16 | 16 | 16 | 15 | 17 |
| average ± S.D. | | 15.7 ± 0.9 | 15.2 ± 0.5 | 15.5 ± 1.0 | 15.7 ± 0.5 | 15.7 ± 0.5 | 16.2 ± 0.9 | 16.7 ± 0.5 |
| Eye-drops with 0.5% timolol | | | | | | | | |
| 101 | RE | 16 | 15 | 14 | 14 | 15 | 16 | 16 |
| 102 | RE | 16 | 14 | 13 | 14 | 15 | 16 | 17 |
| 103 | RE | 16 | 15 | 13 | 15 | 16 | 17 | 16 |
| 104 | RE | 15 | 15 | 14 | 15 | 16 | 15 | 15 |
| average ± S.D. | | 15.7 ± 0.5 | 14.7 ± 0.5 | 13.5 ± 0.6 | 14.5 ± 0.6 | 15.5 ± 0.6 | 16.0 ± 0.6 | 16.0 ± 0.8 |
| Eye-drops with 0.050% flunarizine and 0.5% timolol (MEG 02) | | | | | | | | |
| 105 | RE | 16 | 14 | 13 | 14 | 15 | 16 | 16 |
| 106 | RE | 17 | 13 | 14 | 14 | 14 | 15 | 17 |
| 107 | RE | 16 | 14 | 12 | 14 | 15 | 16 | 16 |
| 108 | RE | 16 | 14 | 12 | 13 | 14 | 15 | 15 |
| average ± S.D. | | 16.2 ± 0.5 | 13.7 ± 0.5 | 12.7 ± 1.0 | 13.7 ± 0.5 | 14.5 ± 0.6 | 15.5 ± 0.6 | 16.2 ± 0.5 |
| Eye-drops with 0.050% flunarizine and 0.5% betaxolol | | | | | | | | |
| 109 | RE | 15 | 14 | 14 | 14 | 15 | 16 | 15 |
| 110 | RE | 16 | 14 | 14 | 14 | 16 | 16 | 17 |
| 111 | RE | 17 | 15 | 15 | 16 | 16 | 16 | 17 |
| 112 | RE | 17 | 16 | 15 | 15 | 16 | 16 | 16 |
| average ± S.D. | | 16.2 ± 1.0 | 14.7 ± 1.0 | 14.5 ± 0.6 | 14.7 ± 1.0 | 15.7 ± 0.5 | 16.0 ± 0 | 16.2 ± 1.0 |
| Eye-drops with 0.050% flunarizine and 2.0% carteolol | | | | | | | | |
| 113 | RE | 17 | 16 | 14 | 15 | 16 | 17 | 16 |
| 114 | RE | 16 | 15 | 15 | 15 | 16 | 16 | 16 |
| 115 | RE | 16 | 13 | 14 | 15 | 16 | 16 | 17 |
| 116 | RE | 15 | 12 | 14 | 15 | 15 | 16 | 16 |
| average ± S.D. | | 16.0 ± 0.8 | 14.0 ± 1.8 | 14.2 ± 0.5 | 15.0 ± 0.0 | 15.7 ± 0.5 | 16.2 ± 0.5 | 16.2 ± 0.5 |

From the experimental results of the previous table it appears on one hand that, in the conditions of the test, flunarizine alone had a better performance in lowering the intraocular pressure than timolol alone. On the other hand, the data show that that the activity of flunarizine was further enhanced by the addition of timolol in the formulation, as At the end of the quarantine period the rabbits were anaesthetised by intramuscular administration of ketamine hydrochloride and xylazine hydrochloride (RBI). The right eye was gently pushed outwardly after instilling 25 μl of Novesine® eye-drops, containing oxybuprocaine as an anaesthetic; then, a sterile solution of σ-chymotrypsin (SIGMA, Milan; 150 units in 100 μl of physiologic sterile solution) was injected in the posterior chamber of the right eye by means of a 30G sterile needle. After the administration of the enzyme, the eye was thoroughly washed with physiologic sterile solution in order to remove any traces of α-chymotrypsin which could damage the ocular tissues. Then, 2 drops of a commercial ophthalmic antibiotic solution (Colbiocin®, SIFI S.p.A., containing chloramphenicol, rolitetracycline, colistin methanesulphonate) were instilled. The treatment was carried out 3 times a day (at 8.00 a.m., 12.00 a.m. and 6.00 p.m.) for one week after the administration of α-chymotrypsin. The rabbits were employed in the tests after one month from the induction of ocular hypertension by means of the enzyme.

The rabbits, divided also in this case in groups of 4 animals, were treated by instillation of 50 μl of the product under test in the right conjunctival fornix. In a first experiment the agents employed were the same as in the first test reported in the foregoing (MEG 01 eye-drops with 0,050% flunarizine, placebo, and eye-drops with 0,056% verapamil, 0,051% diltiazem and 0,043% nifedipine respectively).

The intraocular pressure in the treated eye was measured, according to the same procedure as in the previous tests, 15 minutes before the instillation of the eye-drops and 30, 60, 90, 120, 180 and 240 minutes after. The values obtained were statistically analysed according to the criteria mentioned in the foregoing.

The following table shows, for each test group, both the individual intraocular pressure responses and their average values (± standard deviation). The average values of the intraocular pressure reduction, expressed in terms of percentage, are also diagrammatically translated into the graph of FIG. 1.

TABLE 3

Intraocular pressure in rabbits with normal pressure treated with the tested agents

| Rabbit No. | Eye | Intraocular pressure (mmHg) at the time (min) | | | | | | |
|---|---|---|---|---|---|---|---|---|
| | | 0 | 30 | 60 | 90 | 120 | 180 | 240 |
| Eye-drops with 0.050% flunarizine (MEG 01) | | | | | | | | |
| 21 | RE | 57 | 47 | 45 | 50 | 51 | 56 | 56 |
| 22 | RE | 46 | 38 | 37 | 38 | 39 | 44 | 45 |
| 23 | RE | 36 | 30 | 28 | 32 | 34 | 37 | 37 |
| 24 | RE | 52 | 43 | 41 | 43 | 45 | 51 | 51 |
| average ± S.D. | | 47.7 ± 9.03 | 39.5 ± 7.32 | 37.7 ± 7.25 | 40.7 ± 7.63 | 42.2 ± 7.36 | 47.0 ± 8.28 | 47.25 ± 8.18 |
| Placebo | | | | | | | | |
| 25 | RE | 57 | 56 | 57 | 58 | 56 | 57 | 57 |
| 26 | RE | 47 | 48 | 46 | 47 | 48 | 48 | 47 |
| 27 | RE | 41 | 42 | 43 | 42 | 41 | 42 | 43 |
| 28 | RE | 52 | 50 | 51 | 51 | 50 | 53 | 52 |
| average ± S.D. | | 49.25 ± 6.84 | 49.0 ± 5.77 | 49.25 ± 6.13 | 49.5 ± 6.75 | 48.75 ± 6.18 | 50.0 ± 6.48 | 49.7 ± 6.07 |
| Eye-drops with 0.056% verapamil | | | | | | | | |
| 29 | RE | 56 | 55 | 56 | 55 | 55 | 57 | 56 |
| 30 | RE | 47 | 48 | 49 | 46 | 47 | 46 | 48 |
| 31 | RE | 42 | 40 | 43 | 41 | 41 | 42 | 43 |
| 32 | RE | 51 | 52 | 52 | 50 | 51 | 50 | 51 |
| average ± S.D. | | 49.0 ± 5.94 | 48.7 ± 6.5 | 50.0 ± 5.47 | 48.0 ± 5.94 | 48.5 ± 5.97 | 48.75 ± 6.39 | 49.5 ± 5.44 |
| Eye-drops with 0.051% diltiazem | | | | | | | | |
| 33 | RE | 55 | 55 | 53 | 54 | 56 | 56 | 55 |
| 34 | RE | 52 | 53 | 51 | 52 | 52 | 51 | 52 |
| 35 | RE | 47 | 48 | 46 | 46 | 47 | 48 | 47 |
| 36 | RE | 42 | 42 | 40 | 41 | 43 | 43 | 41 |
| average ± S.D. | | 49.0 ± 5.71 | 49.5 ± 5.80 | 47.5 ± 5.80 | 48.2 ± 5.90 | 49.5 ± 5.68 | 49.0 ± 5.71 | 48.7 ± 6.13 |
| Eye-drops with 0.043% nifedipine | | | | | | | | |
| 37 | RE | 54 | 55 | 53 | 52 | 53 | 54 | 54 |
| 38 | RE | 50 | 52 | 50 | 50 | 49 | 48 | 49 |
| 39 | RE | 47 | 45 | 45 | 46 | 46 | 45 | 47 |
| 40 | RE | 41 | 39 | 39 | 38 | 40 | 41 | 42 |
| average ± S.D. | | 48.0 ± 5.47 | 47.7 ± 7.18 | 46.75 ± 6.13 | 46.5 ± 6.19 | 47.0 ± 5.47 | 48.00 ± 4.98 | 48.00 ± 4.96 |

Table 3 shows that the administration of the vehicle alone does not result in any significant variation in the intraocular pressure, while MEG 01 with 0.050% flunarizine) caused a reduction in the intraocular pressure remarkably higher than that obtainable with the administration of the other calcium antagonists tested. As it may be observed, the values of intraocular pressure in rabbits with ocular hypertension after treatment with ophthalmic solutions containing equivalent amounts of verapamil, diltiazem or nifedipine, in the same vehicle as MEG 01, do not show any significant reduction.

Figure 2:
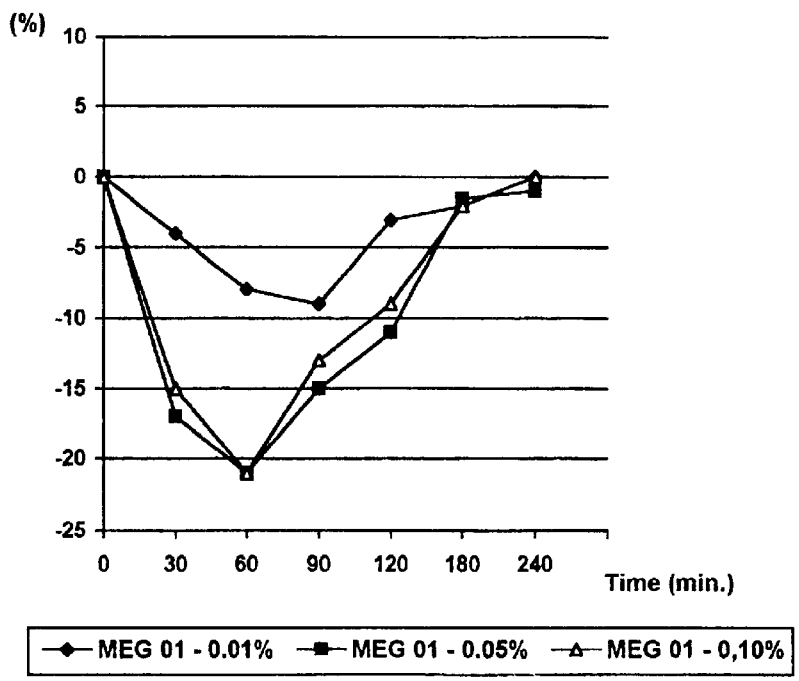
FIG. 2 shows the percent reduction in the intraocular pressure obtained upon instillation, in the eyes of rabbits with ocular hypertension, of flunarizine at various concentrations.

In a second series of trials, employing identical procedure steps, the ophthalmic solution according to the invention was tested at different concentrations of flunarzine, i.e. 0.1% and 0.01% by weight of active ingredient. The aim was to compare the response so obtained with the response observed with the MEG 01 eye-drops containing 0.05 wt. % flunarizine. The results are presented in the following table, and are also illustrated (as average percent amounts of the intraocular pressure reduction detected) in the graph of FIG. 2.

TABLE 4

Intraocular pressure in rabbits with ocular hypertension treated with flunarizine

| Rabbit No. | Eye | Intraocular pressure (mmHg) at the time (min) | | | | | | |
|---|---|---|---|---|---|---|---|---|
| | | 0 | 30 | 60 | 90 | 120 | 180 | 240 |
| Eye-drops with 0.010% flunarizine | | | | | | | | |
| 41 | RE | 60 | 58 | 55 | 53 | 58 | 60 | 61 |
| 42 | RE | 65 | 61 | 59 | 60 | 62 | 64 | 65 |
| 43 | RE | 53 | 51 | 49 | 48 | 52 | 52 | 52 |
| 44 | RE | 52 | 50 | 48 | 49 | 51 | 50 | 52 |
| average ± S.D. | | 57.5 ± 6.13 | 55.0 ± 5.35 | 52.7 ± 5.18 | 52.5 ± 5.44 | 55.7 ± 5.18 | 56.5 ± 6.60 | 57.5 ± 6.55 |
| Eye-drops with 0.050% flunarizine | | | | | | | | |
| 21 | RE | 57 | 47 | 45 | 50 | 51 | 56 | 56 |
| 22 | RE | 46 | 38 | 37 | 38 | 39 | 44 | 45 |
| 23 | RE | 36 | 30 | 28 | 32 | 34 | 37 | 37 |
| 24 | RE | 52 | 43 | 41 | 43 | 45 | 51 | 51 |
| average ± S.D. | | 47.7 ± 9.03 | 39.5 ± 7.32 | 37.7 ± 7.27 | 40.7 ± 7.63 | 42.2 ± 7.36 | 47.0 ± 8.28 | 47.2 ± 8.18 |
| Eye-drops with 0.100% flunarizine | | | | | | | | |
| 45 | RE | 58 | 48 | 45 | 49 | 51 | 56 | 57 |
| 48 | RE | 48 | 40 | 38 | 41 | 43 | 47 | 49 |
| 47 | RE | 42 | 36 | 34 | 36 | 38 | 41 | 43 |
| 48 | RE | 51 | 45 | 40 | 46 | 48 | 50 | 50 |
| average ± S.D. | | 49.7 ± 6.6 | 42.2 ± 5.31 | 39.2 ± 4.57 | 43.0 ± 5.71 | 45.0 ± 5.71 | 48.5 ± 6.24 | 49.7 ± 5.73 |

From the foregoing table it may be observed that the highest percent reduction in the intraocular pressure was shown by the MEG 01 preparation with 0.05% flunarizine, while the preparation with the highest concentration (0.1%) showed an activity comparable with that of the 0.05% preparation. This is shown more clearly in the graph of FIG. 2.

In a further series of tests the activity of combinations of flunarizine with a beta-blocking agent was tested on rabbits with hypertension. The experimental conditions were exactly the same as before. Three groups of animals were treated with the compositions defined under f), g) and h) in the previous section, and the results obtained are summarised in the following table. Also in this case, the data already obtained in the same experimental conditions for flunarizine alone and for the placebo are repeated for ease of comparison.

TABLE 5

Intraocular pressure in rabbits with ocular hypertension treated with the tested agents

| Rabbit No. | Eye | Intraocular pressure (mmHg) at the time (min) | | | | | | |
|---|---|---|---|---|---|---|---|---|
| | | 0 | 30 | 60 | 90 | 120 | 180 | 240 |
| Eye drops with 0.050% flunarizine (MEG 01) | | | | | | | | |
| 21 | RE | 57 | 47 | 45 | 50 | 51 | 56 | 56 |
| 22 | RE | 46 | 38 | 37 | 38 | 39 | 44 | 45 |
| 23 | RE | 36 | 30 | 28 | 32 | 34 | 37 | 37 |
| 24 | RE | 52 | 43 | 41 | 43 | 45 | 51 | 51 |
| average ± S.D. | | 47.7 ± 9.0 | 39.5 ± 7.3 | 37.7 ± 7.2 | 40.7 ± 7.6 | 42.2 ± 7.4 | 47.0 ± 8.3 | 47.2 ± 8.2 |
| Placebo | | | | | | | | |
| 25 | RE | 57 | 56 | 57 | 58 | 56 | 57 | 57 |
| 26 | RE | 47 | 48 | 46 | 47 | 48 | 48 | 47 |
| 27 | RE | 41 | 41 | 43 | 42 | 41 | 42 | 43 |
| 28 | RE | 52 | 50 | 51 | 51 | 50 | 53 | 52 |
| average ± S.D. | | 49.2 ± 6.8 | 49.0 ± 5.8 | 49.2 ± 6.1 | 49.5 ± 6.7 | 48.7 ± 6.2 | 50.0 ± 6.5 | 49.7 ± 6.1 |
| Eye-drops with 0.5% timolol | | | | | | | | |
| 117 | RE | 53 | 43 | 42 | 42 | 46 | 52 | 53 |
| 118 | RE | 54 | 45 | 42 | 42 | 45 | 48 | 51 |
| 119 | RE | 46 | 39 | 39 | 38 | 39 | 42 | 45 |
| 120 | RE | 43 | 40 | 36 | 37 | 40 | 42 | 44 |
| average ± S.D. | | 49.0 ± 5.3 | 41.7 ± 4.7 | 39.7 ± 2.9 | 39.7 ± 2.6 | 42.5 ± 3.5 | 46.0 ± 4.9 | 48.2 ± 4.4 |
| Eye drops with 0.050% flunarizine and 0.5% timolol (MEG 02) | | | | | | | | |
| 121 | RE | 52 | 35 | 33 | 33 | 36 | 38 | 41 |
| 122 | RE | 58 | 39 | 36 | 37 | 41 | 46 | 48 |
| 123 | RE | 47 | 31 | 29 | 32 | 35 | 37 | 38 |
| 124 | RE | 45 | 32 | 26 | 30 | 36 | 36 | 35 |

TABLE 5-continued

Intraocular pressure in rabbits with ocular hypertension treated with the tested agents

| Rabbit No. | Eye | Intraocular pressure (mmHg) at the time (min) | | | | | | |
|---|---|---|---|---|---|---|---|---|
| | | 0 | 30 | 60 | 90 | 120 | 180 | 240 |
| average ± S.D. | | 50.5 ± 5.8 | 34.2 ± 3.6 | 31.0 ± 4.4 | 33.0 ± 2.9 | 37.0 ± 2.7 | 39.2 ± 4.6 | 40.5 ± 5.6 |
| Eye-drops with 0.050% flunarizine and 0.5% betaxolol | | | | | | | | |
| 125 | RE | 49 | 39 | 36 | 38 | 42 | 42 | 43 |
| 126 | RE | 45 | 35 | 37 | 37 | 39 | 40 | 41 |
| 127 | RE | 56 | 44 | 42 | 46 | 47 | 49 | 49 |
| 128 | RE | 55 | 45 | 41 | 43 | 47 | 46 | 51 |
| average ± S.D. | | 51.2 ± 5.2 | 40.7 ± 4.6 | 39.0 ± 2.9 | 41.0 ± 4.2 | 43.7 ± 3.9 | 44.2 ± 4.0 | 46.0 ± 4.8 |
| Eye-drops with 0.050% flunarizine and 2.0% carteolol | | | | | | | | |
| 129 | RE | 57 | 53 | 40 | 42 | 50 | 54 | 56 |
| 130 | RE | 52 | 46 | 44 | 45 | 48 | 49 | 49 |
| 131 | RE | 47 | 37 | 39 | 40 | 44 | 43 | 43 |
| 132 | RE | 46 | 36 | 37 | 39 | 40 | 41 | 43 |
| average ± S.D. | | 50.5 ± 5.1 | 43.0 ± 8.0 | 40.0 ± 2.9 | 41.5 ± 2.6 | 45.5 ± 4.4 | 46.7 ± 5.9 | 47.7 ± 6.2 |

Figure 3:
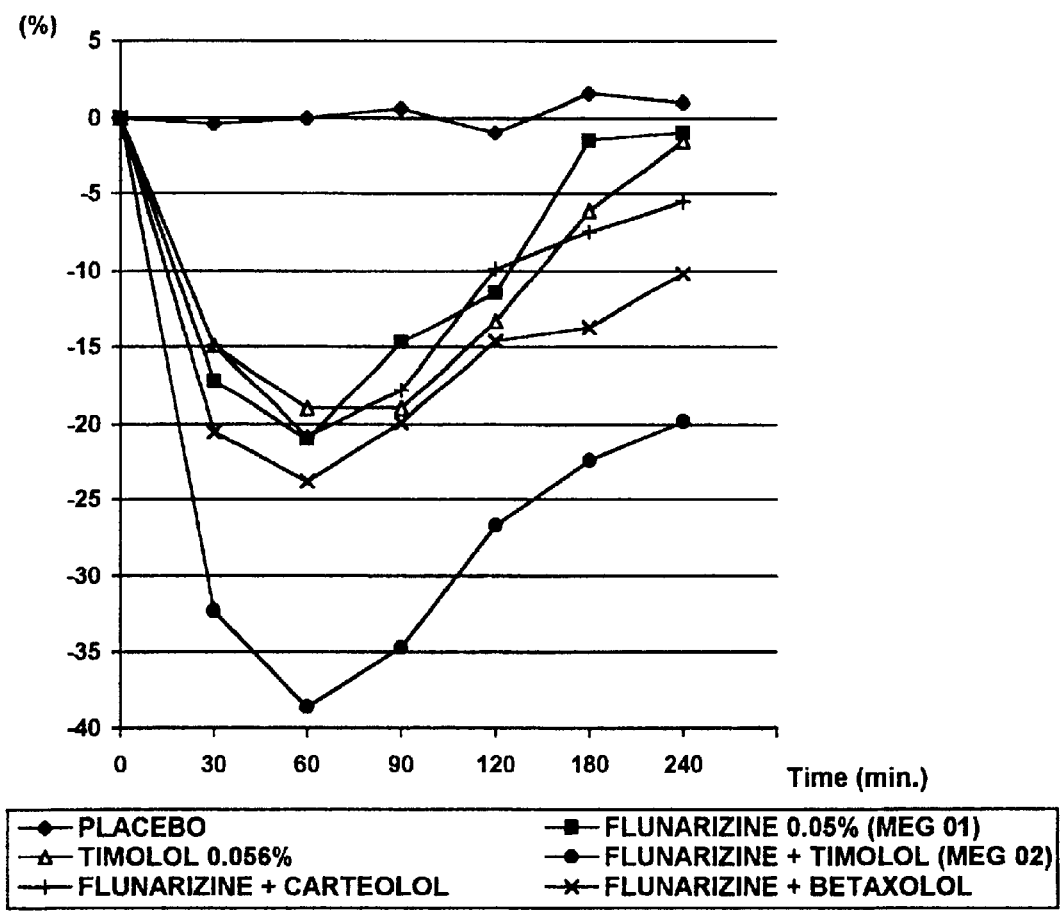
FIG. 3 shows the percent reduction in the intraocular pressure obtained upon instillation, in the eyes of rabbits with ocular hypertension, of flunarizine in combination with various beta-blocking agents.

The data reported in Table 5, and even more clearly the diagram of FIG. 3, evidence the remarkable activity of the combination of flunarizine with timolol and, in general, the good performance of the combinations of flunarizine with beta-blocking agents. Also in this case, flunarizine alone showed an effectiveness comparable to or better than that of timolol alone.

Toxicity Studies a. Evaluation of the Corneal Swelling

The evaluation of the thickness of the cornea was carried out ecographically by means of a UBM System 840 (Humphrey Instruments, San Leandro, Calif., USA). The apparatus includes a 50 MHz probe and allows to visualise images on a display with a resolution of about 504 and a visualisation field of 5×5 mm. The software incorporated allows to modify the focalisation depth of the ultrasound beam, and to capture the image while varying its amplification.

The animals employed in this test were of the same type as those described in the foregoing, and were treated in the same way. The test was carried out, after having anaesthetised the animal (with ketamine hydrochloride and xylazine hydrochloride), by placing into contact with the eyeball tiny cups filled in with a coupling means (ultrasound gel). The rabbits received in the right eye a single instillation (50 µl) of each of the same agents employed in the pharmacodinamic studies: a) MEG 01 eye-drops with 0.050% flunarizine, c) eye-drops containing 0.056 wt. % verapamil; d) eye-drops containing 0.051 wt. % diltiazem; d) eye-drops containing 0.043 wt. % nifedipine. In the left eye the rabbits received an instillation of an equal amount of placebo (vehicle of MEG 01 without any active ingredient).

The following table shows the corneal thickness as detected on various groups of 4 rabbits each, before the instillation and at fixed time intervals after the instillation.

TABLE 6

Corneal thickness in rabbits topically treated with calcium antagonists

| Rabbit No | Eye | Corneal thickness (mm) at the time (min) | | | |
|---|---|---|---|---|---|
| | | Baseline | 1 hour | 2 hours | 3 hours |
| RE: MEG 01 with 0.050% flunarizine - LE: Placebo | | | | | |
| 49 | RE | 0.394 | 0.394 | 0.394 | 0.394 |
| 49 | LE | 0.394 | 0.394 | 0.394 | 0.394 |
| 50 | RE | 0.347 | 0.347 | 0.347 | 0.347 |
| 50 | LE | 0.347 | 0.347 | 0.347 | 0.347 |
| 51 | RE | 0.386 | 0.386 | 0.386 | 0.386 |
| 51 | LE | 0.386 | 0.386 | 0.386 | 0.386 |
| 52 | RE | 0.363 | 0.363 | 0.363 | 0.363 |
| 52 | LE | 0.363 | 0.363 | 0.363 | 0.363 |
| RE: eye-drops with 0.056% verapamil - LE: Placebo | | | | | |
| 53 | RE | 0.356 | 0.376 | 0.385 | 0.383 |
| 53 | LE | 0.356 | 0.358 | 0.360 | 0.367 |
| 54 | RE | 0.384 | 0.398 | 0.406 | 0.402 |
| 54 | LE | 0.384 | 0.382 | 0.388 | 0.380 |
| 55 | RE | 0.372 | 0.387 | 0.400 | 0.402 |
| 55 | LE | 0.372 | 0.374 | 0.368 | 0.372 |
| 58 | RE | 0.392 | 0.401 | 0.494 | 0.410 |
| 56 | LE | 0.392 | 0.390 | 0.396 | 0.388 |
| RE: eye-drops with 0.051% diltiazem - LE: Placebo | | | | | |
| 57 | RE | 0.377 | 0.380 | 0.382 | 0.384 |
| 57 | LE | 0.377 | 0.380 | 0.380 | 0.377 |
| 58 | RE | 0.389 | 0.392 | 0.394 | 0.396 |
| 58 | LE | 0.389 | 0.389 | 0.325 | 0.387 |
| 59 | RE | 0.396 | 0.400 | 0.400 | 0.400 |
| 59 | LE | 0.396 | 0.396 | 0.394 | 0.398 |
| 60 | RE | 0.358 | 0.362 | 0.364 | 0.364 |
| 60 | LE | 0.358 | 0.358 | 0.360 | 0.360 |
| RE: eye-drops with 0.043% nifedipine - LE: Placebo | | | | | |
| 61 | RE | 0.375 | 0.380 | 0.380 | 0.380 |
| 61 | LE | 0.375 | 0.375 | 0.376 | 0.375 |
| 62 | RE | 0.372 | 0.380 | 0.378 | 0.378 |
| 62 | LE | 0.372 | 0.374 | 0.372 | 0.372 |
| 63 | RE | 0.396 | 0.398 | 0.400 | 0.400 |
| 63 | LE | 0.396 | 0.396 | 0.396 | 0.396 |
| 64 | RE | 0.384 | 0.388 | 0.389 | 0.390 |
| 64 | LE | 0.384 | 0.382 | 0.984 | 0.382 |

As it may be observed from the foregoing data, with the use of the product according to the invention no alteration has been detected in the corneal thickness for the whole period of the test. On the contrary, the ophthalmic solution containing 0.056% verapamil caused corneal swelling, with increases in thickness of about 15–20 μm/hour. No significant effect has been noted for the eye-drops containing diltiazem (only slight swelling) or nifedipine.

b. Acute Tolerability

In order to evaluate the tolerability of the calcium channel blocking agent according to the invention when topically applied to the eye, rabbits (of the same kind as those employed in the previous experimentation) were treated as follows, after an initial acclimatation period. On the first day, 12 instillations of MEG 01 (0.05%) in the right conjunctival fornix, of 0.05 ml each, were made at intervals of 30 minutes. The contralateral eye was treated with placebo and served as a control.

The condition of the ocular tissues was observed according to the Draize modified test (Spampinato S., Marino A., Bucolo C., Canossa M., Bachetti T., Mangiafico S., Effect of sodium naproxen eye drops on rabbit ocular inflammation induced by sodium arachidonate, J. Ocular Pharm., 7 (2); 125–133, (1991)). The examination was carried out every hour starting from the first administration for 7 hours, and then 24, 48 and 72 hours after the last treatment, giving arbitrary scores to the various aspects of the palpebral and bulbar conjunctiva, of the iris and of the cornea.

No significant reddening of the conjunctiva was observed for the whole period of the test, both in the eyes treated with MEG 01 eye-drops (0.05% wt. % flunarizine) and in the eyes treated with placebo. No oedema was detected in any of the eyes tested. In addition, no alteration involving the iris was noted in any of the eyes treated, and the presence of drain material was maintained at a normal level. Neither any damage has been detected in the corneal tissues; two eyes only showed a slight desepithelisation.

The results obtained show that the MEG 01 ophthalmic solution based on 0.05% flunarizine is well tolerated in the rabbit eye after repeated instillation in the conjunctival fornix.

Binding Studies

The receptor binding technique was carried out on cell membranes obtained from the irido-ciliary body complex explanted, after sacrifice, from male albino rabbits of the New Zealand strain (Charles River Italiana, of Calco (CO)). The tissue was homogenised in buffer and the $P_2$ fraction, rich in cell membrane proteins, was isolated. The said fraction was obtained by centrifugation according to what described in the literature (Mach R. H., Smith C. R., Childers S. R. Ibogaine possesses a selective affinity for sigma 2 receptors, Life Sci. 57(4); 5742). The La total protein concentration was determined with the Lowry method.

Aliquots of the $P_2$ fraction of the homogenate respectively containing 300 μg of total proteins were incubated in polypropylene test tubes containing scalar amounts of the calcium antagonists under test (i.e. flunarizine, verapamil, nifedipine and nimodipine), and a known amount of 3H(+)-N-allyl-nor-methazocine (SKF) (experimentally used as a a ligand). The non specific binding was evaluated in presence of haloperidol.

All tests were carried out in duplicate. The reaction was maintained at 37° C. for 150 minutes, followed by filtration on WhatmannGF/B filters. The radioactivity left on the filters was measured by liquid scintillation spectrometry. The $IC_{50}$ was determined, and the results obtained are shown in the following table.

TABLE 7

Effects of various calcium antagonists on the inhibition of $^3H(+)$-N-allyl-nor-methazocine binding

| Substance | $IC_{50}$ (nM) |
|---|---|
| flunarizine | 23.9 |
| verapamil | >10,000 |
| nifedipine | >10,000 |
| nimodipine | >10,000 |
| diltiazem | >10,000 |

The preceding data confirm the findings of the research that lead to the present invention, which have been discussed in the introduction. Namely, the data show that flunarizine has an affinity on σ-1 receptors, as opposed to the other more known and studied calcium channel blocking agents, such as verapamil, nifedipine and diltiazem. This finding suggests that the σ-1 receptors are involved in the mechanism responsible of the intraocular pressure decrease caused by flunarizine, and that this particular feature is responsible of the surprisingly higher activity of flunarizine as an anti-glaucoma agent for topical use.

The present invention has been disclosed with particular reference to some specific embodiments thereof, but it should be understood that modifications and changes may be made by the persons skilled in the art without departing from the scope of the invention as defined in the appended claims.

What is claimed is:

1. Method for lowering ocular hypertension, comprising administering, to a patient in need thereof, a topical ophthalmic medicament containing flunarizine or a pharmaceutically acceptable salt thereof.

2. Method according to claim 1, wherein said topical ophthalmic medicament is in the form of an aqueous solution or suspension, or in the form a gel, an ointment or a cream in a pharmaceutically acceptable ophthalmic vehicle, or in the form of an erodible ocular insert or of a "reservoir" system with a polymer membrane, to be placed in the conjunctival sac.

3. Method according to claim 1, wherein the flunarizine concentration in said ophthalmic medicament is from 0.0001 to 0.500% by weight.

4. Method according to claim 1, wherein the flunarizine concentration is 0.050% by weight.

5. Method according to claim 1, wherein flunarizine is present in the said ophthalmic medicament in the form of its hydrochloride salt.

6. Method according to claim 1, wherein said topical ophthalmic medicament further contains a beta-blocking agent.

7. Method according to claim 6, wherein the concentration of beta-blocking agent in said ophthalmic medicament is from 0.1 to 2.5% by weight.

8. Method according to claim 6, wherein said beta-blocking agent is timolol or a pharmaceutically acceptable salt thereof.

9. Method according to claim 1, wherein said topical ophthalmic medicament is in the form of an aqueous solution and further contains one or more tonicity adjusting agents, one or more buffers and one or more antioxidants.

10. Method according to claim 1, wherein said topical ophthalmic medicament further contains one or more agents improving the ocular tolerability chosen from cyclodextrins, polysorbate 80 (or Tween 80), dextrane, polyethylene glycol and poloxamers.

11. Method according to claim 1, wherein said topical ophthalmic medicament further contains one or more preservatives or antimicrobial agents.

* * * * *